(12) United States Patent
Hillios et al.

(10) Patent No.: US 7,789,856 B2
(45) Date of Patent: Sep. 7, 2010

(54) INJECTION AID AND STABILITY DISK FOR SYRINGE OR INSULIN PEN

(76) Inventors: Christopher H. Hillios, 81 Gunn Rd., Southampton, MA (US) 01073; Sonia Hillios, 81 Gunn Rd., Southampton, MA (US) 01073

( * ) Notice: Subject to any disclaimer, the term of this patent is extended or adjusted under 35 U.S.C. 154(b) by 181 days.

(21) Appl. No.: 11/747,375

(22) Filed: May 11, 2007

(65) Prior Publication Data

US 2007/0265575 A1    Nov. 15, 2007

Related U.S. Application Data

(60) Provisional application No. 60/747,238, filed on May 15, 2006.

(51) Int. Cl.
    *A61M 5/00*    (2006.01)
(52) U.S. Cl. ....................................... 604/117
(58) Field of Classification Search ................. 604/162, 604/163, 115, 116, 117
    See application file for complete search history.

(56) References Cited

U.S. PATENT DOCUMENTS

| | | | |
|---|---|---|---|
| 1,274,081 A | 7/1918 | Riethmueller | |
| 1,453,309 A | 5/1923 | Eberly, Jr. | |
| 1,774,707 A | 9/1930 | Gau | |
| 1,934,046 A | 11/1933 | Demarchi | |
| 2,001,638 A | 5/1935 | Tornsjo | |
| 2,238,323 A | 4/1941 | Hollingsworth | |
| 2,338,800 A | 1/1944 | Burke | |
| 2,578,812 A | 12/1951 | Kollsman | |
| 3,306,291 A * | 2/1967 | Burke | 604/110 |
| 3,400,715 A | 9/1968 | Pederson | |
| 3,538,916 A | 11/1970 | Wiles | |
| 3,783,876 A | 1/1974 | Dye | |
| 5,057,087 A * | 10/1991 | Harmon | 604/198 |
| 5,195,526 A * | 3/1993 | Michelson | 600/431 |
| 6,200,291 B1 | 3/2001 | Di Pietro | |
| 6,258,059 B1 | 7/2001 | Weston et al. | |
| 6,569,143 B2 | 5/2003 | Alchas et al. | |

* cited by examiner

*Primary Examiner*—Nicholas D Lucchesi
*Assistant Examiner*—Pritesh Patel (57) ABSTRACT

An injection aid for a syringe includes a disk with a central orifice and a flange. The flange is located on the top of the disk, and surrounds the central orifice. The outlet end or needle hub of a syringe or insulin pen fits in the flange, with the syringe needle extending through the orifice, thereby securing the disk to the syringe. The bottom surface of the disk is generally flat. The bottom surface of the disk makes contact with the skin when the needle is inserted to the proper depth. In other words, the needle lies perpendicular to the disk and is arranged to project past the disk's flat bottom surface by a set, pre-determined length. When the disk is pressed flat against a patient's skin, the needle is at the proper depth for the substance being injected.

13 Claims, 6 Drawing Sheets

INJECTION AID AND STABILITY DISK FOR SYRINGE OR INSULIN PEN

CROSS REFERENCE TO RELATED APPLICATION

This application is entitled to the benefit of and claims priority to U.S. Provisional Application Ser. No. 60/747,238, filed May 15, 2006, the disclosure of which is hereby incorporated by reference herein in its entirety.

FIELD OF THE INVENTION

The present invention relates to surgery and, more particularly, to means for introducing or removing material from the body for therapeutic purposes.

BACKGROUND OF THE INVENTION

The number of patients requiring daily injections is increasing yearly. Both the elderly and children make up a large portion of these patients. Some patients require multiple injections daily. Despite many advances made over the last years, some problems still remain. Fear of needles, shaky hands, and lack of confidence lead to anxiety when injecting. Instability leads to bent needles, increased pain, and difficulty. Existing systems created to help eliminate some of these issues have proven both complicated and costly.

Many of these patients that require injections are diabetic. According to the American Diabetes Association, there are 20.8 million people in the United States alone who have diabetes. This makes up 7% of the American population. Receiving insulin shots at the proper time is important in caring for diabetes. Injection anxiety can hinder the proper timing of insulin shots.

The present invention solves the problems associated with injections and overcomes the disadvantages of existing systems.

SUMMARY OF THE INVENTION

An objective of the invention is to produce a simple, beneficial, yet cost effective solution to the problems associated with syringes and insulin pens.

One embodiment of the present invention relates to a patient or caregiver injection aid for injection by syringe or insulin pen, and in particular to a means for precisely establishing a needle depth for subcutaneous injections. The injection aid comprises a disk with a central orifice and a flange. Located on the top of the disk is the flange, which surrounds the central orifice. The flange is sized to fit the outlet end or needle hub of a syringe or insulin pen, and the syringe or pen needle is inserted through the flange. The flange is designed to secure the disk to the needle hub. The central orifice provides the syringe needle with access to the recipient's skin. The bottom surface of the disk (the skin contacting surface) is generally flat. The bottom surface of the disk makes contact with the skin when the needle is inserted to the proper depth. In other words, the needle lies perpendicular to the disk and is arranged to project past the disk by a set, pre-determined length, wherein when the disk is pressed flat against a patient's skin, the needle is at the proper depth for the substance being injected.

In another embodiment, the injection aid is configured for removable attachment to a syringe or insulin pen, and can be reused. It may be attached to a syringe or pen for use, and then removed after use.

In another embodiment, the disk is a rigid, opaque member that facilitates firm and stable but comfortable contact with a patient while effectively hiding the needle from view, to reduce hesitation and anxiety of needle injection.

In another embodiment, the injection aid can be a permanent fixture to a syringe and, along with the syringe, would be disposed of after use.

In another embodiment, the injection aid is permanently attached or integral with a syringe or other injection device having a permanently attached needle. The needle, syringe body, and injection aid are attached in such a manner that attempting to remove the injection aid (e.g., by manual force) causes the needle to break and/or permanently detach from the syringe body, thereby rendering the injection device inoperable.

The present invention has several benefits. The injection aid provides added confidence and eliminates hesitation on injection because the user focuses on the disk rather than the needle. Because of this, it also lessens pain perception. The injection aid also provides added stability in both filling the syringe and during injection. Furthermore, it eliminates the worry of how far the needle needs to be inserted. The injection aid provides ease of use for both patient and caregiver and enables use in hard to reach areas of the body. Moreover, it is cost-effective.

DETAILED DESCRIPTION OF THE PREFERRED EMBODIMENT

The present invention is an injection aid for injection by syringe, insulin pen, or other needle-based injection device. FIGS. 1-5 illustrate one embodiment of the present invention. The injection aid 2 comprises a rigid disk or other guard 4 having a central orifice 6 and a flange 8. The disk 4 may be opaque in order to prevent the recipient from seeing the needle 18 of the injection device 14. The disk 4 may be any diameter, but will typically be about 1.25 inches in diameter, that is, 1.25±0.25 inches, to facilitate support against the skin without unnecessary unwieldiness. The flange 8, located on the disk's top surface 10, surrounds the central orifice 6. The flange 8 is sized to fit the outlet end 16 of a syringe 14, which allows the injection aid 2 to attach to the syringe 14. The flange 8 secures the disk 4 to the needle/syringe hub 16. The disk's bottom surface 12 is the contacting surface with the skin and may be smooth or slightly textured. A needle 18 of syringe, insulin pen, or injection device 14 is inserted through the flange 8 and passes through central orifice 6 in order to access the recipient's skin. The injection aid 2 may be made of many materials. For example, it may be made of medical grade polymer such as neoprene.

Most commonly, the injection aid is used in conjunction with a disposable medical syringe, meaning those that have a polymer body, a fixed hypodermic needle, and are meant for a single use.

Figure 1:
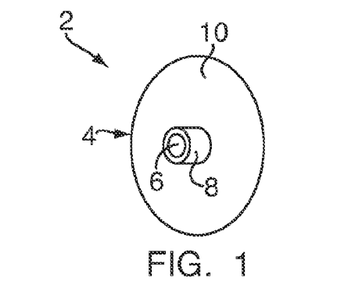
FIG. 1 is an angled front view of one embodiment of the injection aid.
Figure 2A:
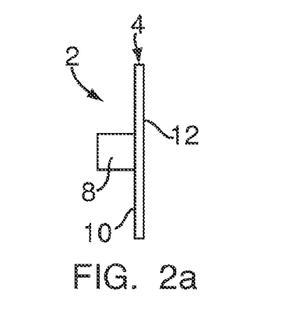
FIGS. 2A and 2B are side views (FIG. 2B in cross section) of an embodiment of the injection aid.
Figure 2B:
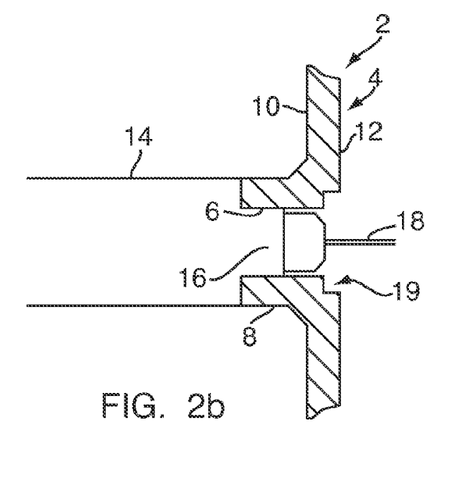
Figure 3:
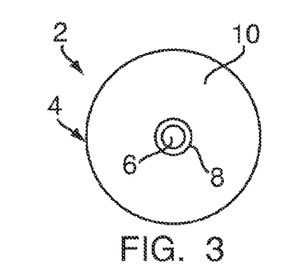
FIG. 3 is a frontal view of an embodiment of the injection aid.
Figure 4:
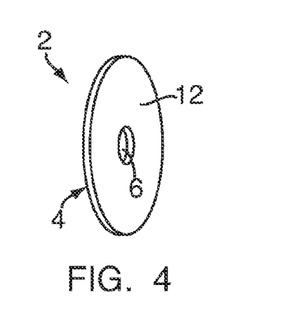
FIG. 4 is an angled back view of an embodiment of the injection aid.
Figure 5:
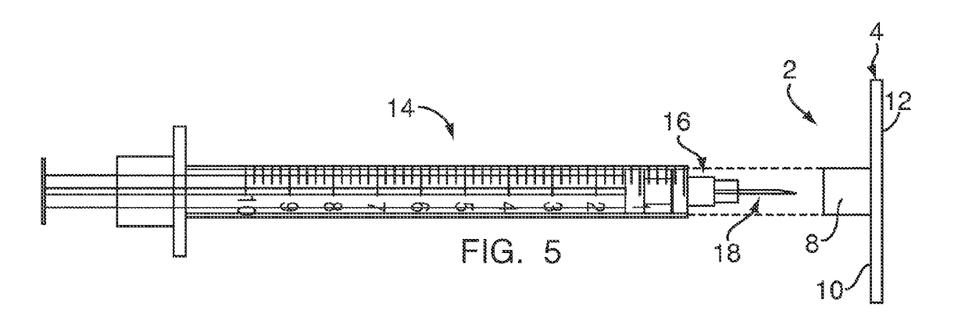
FIG. 5 shows how an embodiment of the injection aid is attached to a syringe.

As indicated in particular in FIG. 2B, the disk 4 may include an annular recess 19 surrounding the central orifice 6, provided for facilitating use of a needle cap or the like.

Figure 6:
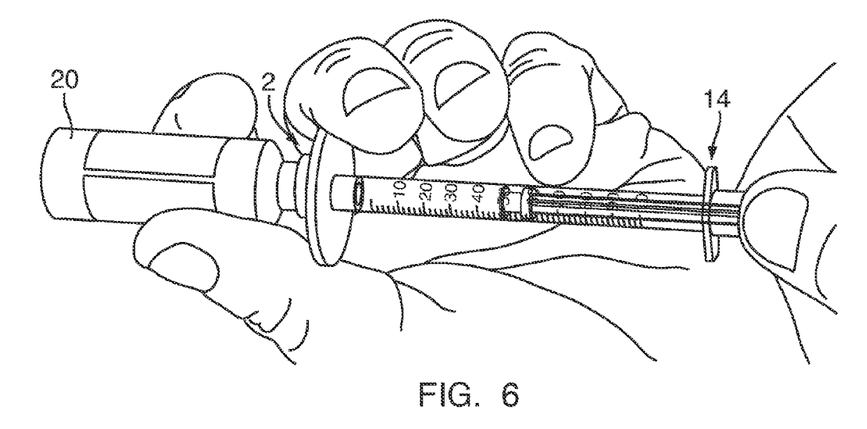
FIG. 6 illustrates an embodiment of the injection aid as used for filling a syringe with insulin.
Figure 7:
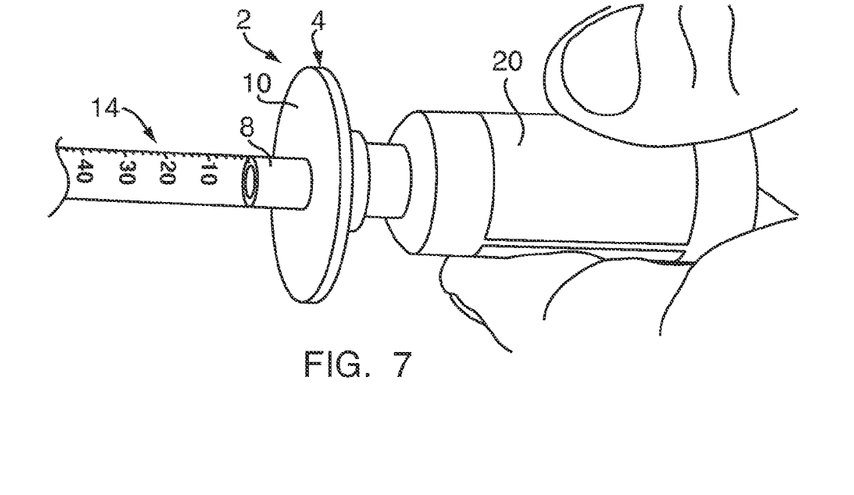
FIG. 7 illustrates another view of an embodiment of the injection aid as used for filling a syringe with insulin.
Figure 8:
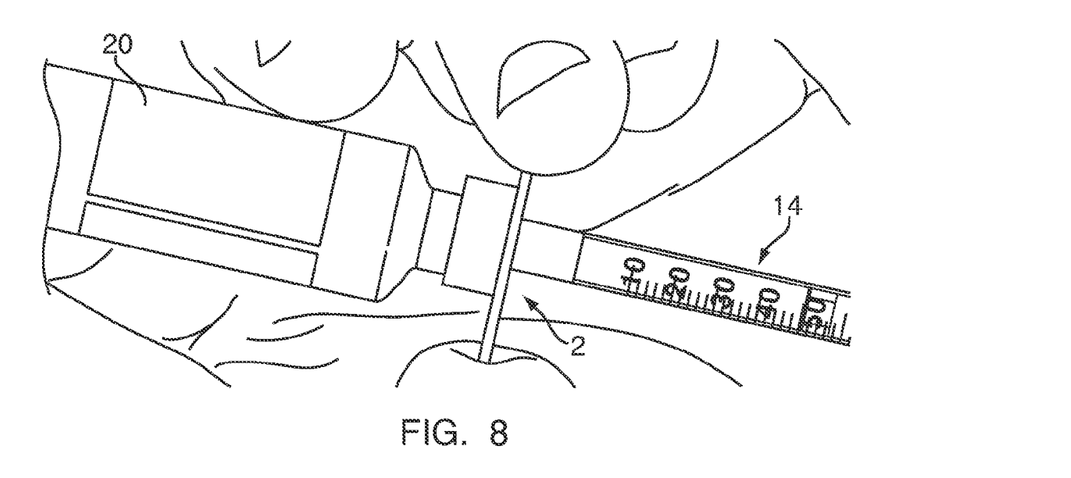
FIG. 8 illustrates another view of an embodiment of the injection aid as used for filling a syringe with insulin.

FIGS. 6-8 illustrate the use of injection aid 2 in filling a syringe 14 with insulin or other drugs from a bottle 20. A needle portion 18 of the syringe 14 is inserted into the bottle 20 until the contact surface 12 touches the top of the bottle 20. The injection aid 2 provides added stability while filling the syringe 14, by shortening the exposed length of the needle 18.

Figure 9:
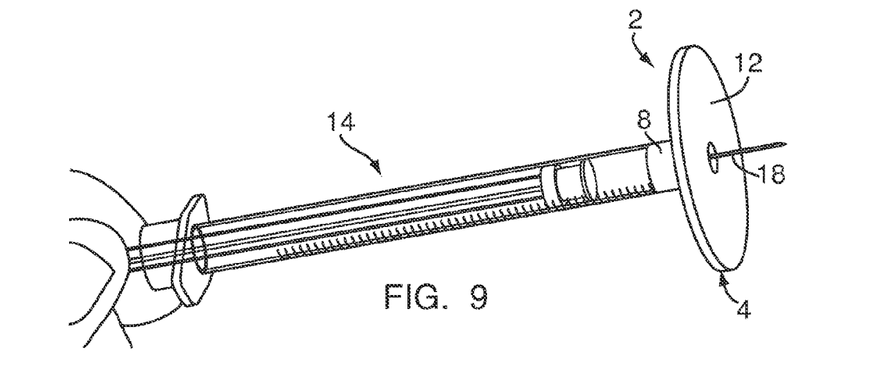
FIGS. 9-12 illustrate various embodiments of the injection aid attached to a syringe.
Figure 10:
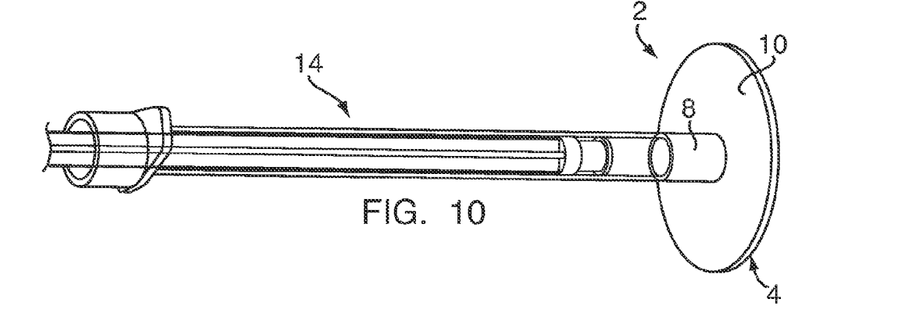
Figure 11:
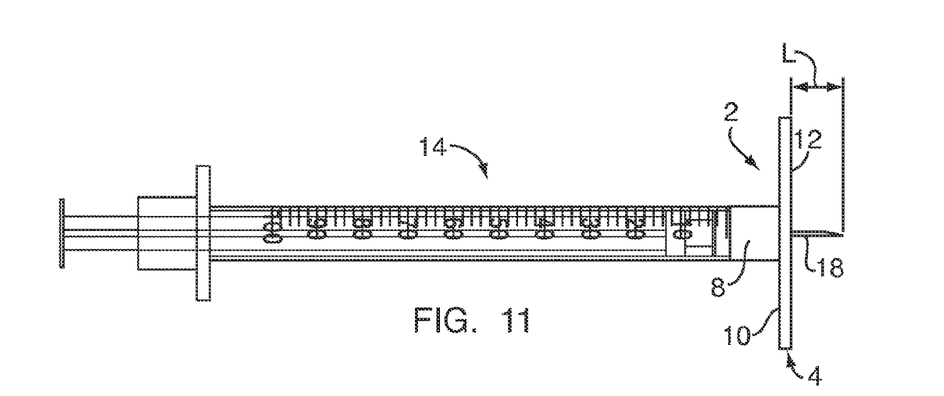

FIGS. 9-11 illustrate the use of injection aid 2 attached to a syringe 14. As described above, the injection aid 2 is attached to a syringe 14 by way of the flange 8. The flange 8 is sized to fit the needle hub 16 of the syringe 14. The needle 18 of the syringe or insulin pen 14 is inserted through the flange 8 and passes through the central orifice 6 in order to access the recipient's skin. The needle 18 is then inserted until the contact surface 12 touches the recipient's skin.

The injection aid 2 provides an added benefit of eliminating user worry about how to find the proper subcutaneous injection depth of the needle 18. The length of the flange 8 may be made to expose a set length "L" of needle 18 (see FIG. 11 and FIG. 13), that is, the needle 18 is perpendicular to the contacting surface 12 and extends past the contacting surface 12 by a set or fixed distance "L." The set length L is chosen to be the proper subcutaneous injection depth for the medication or drug in question, so that the user would simply insert the needle 18 into an injection site until the disk's bottom surface 12 made contact with the recipient's skin. (For example, a syringe and injection aid 2 may be provided in combination to provide a fixed needle depth "L," where "L" is the proper subcutaneous injection depth for the type of medication to be injected using the syringe, e.g., insulin.)

In addition to establishing a set or fixed injection depth, the injection aid 2 is configured to obscure or block a user's view of the needle 18, to facilitate use of the syringe by users who suffer from mild needle anxiety, belonephobia (a more pronounced fear of needles), or related psychological phenomena. Typically, a radius "R" of the disk 4 (see FIG. 13) will be greater than or equal to the distance L that the needle extends out past the bottom surface 12 of the disk 4, to substantially block the needle from view when the syringe is generally viewed from the rear. This relationship may be alternatively expressed in terms of a line "T" defined by a distal tip of the needle and a radially outermost edge of the disk, which forms an angle "β" of at least 45 degrees with respect to the needle.

Figure 12:
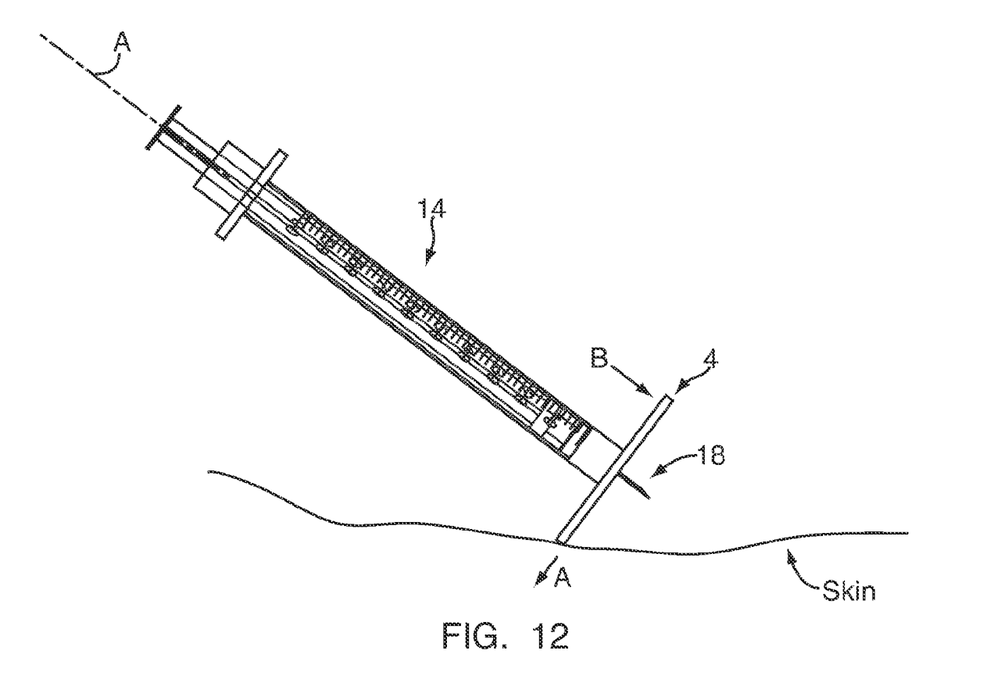
Figure 13:
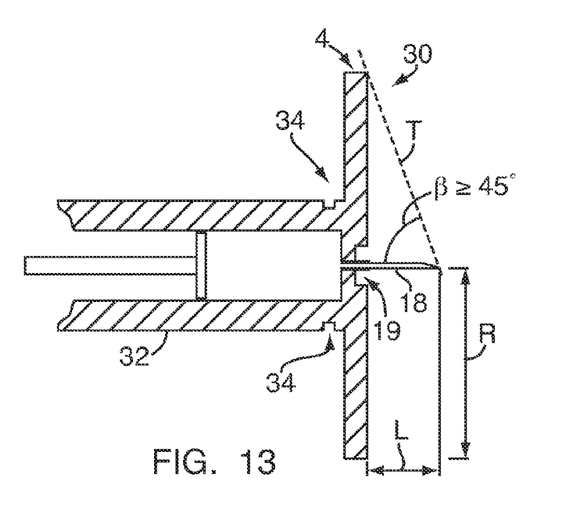
FIG. 13 shows a cross-section view (not to scale) of an injection device with integral, permanently attached injection aid, according to an embodiment of the present invention.
Figure 14A:
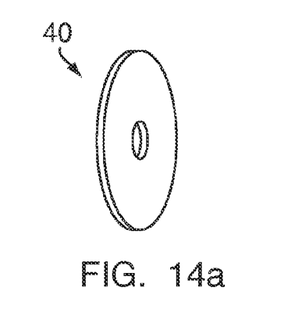
FIGS. 14a-14g show an embodiment of the injection aid 40 for use with an insulin pen 42.
Figure 14B:
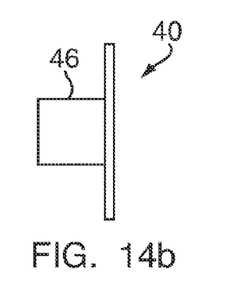
Figure 14C:
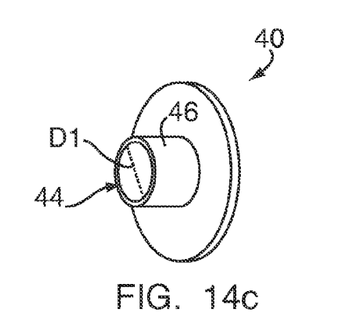
Figure 14D:
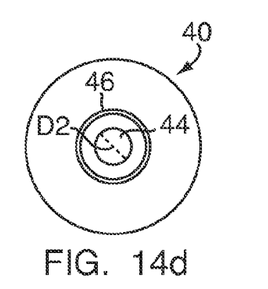
Figure 14E:
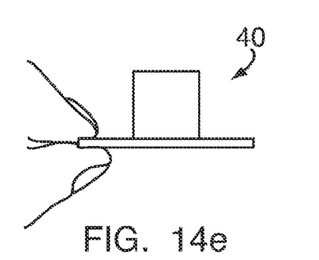
Figure 14F:
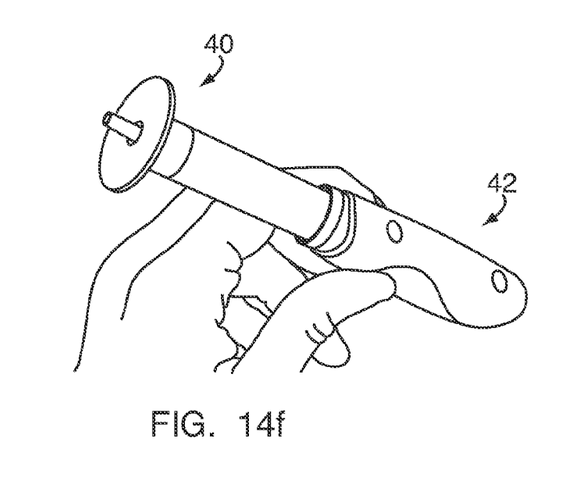
Figure 14G:
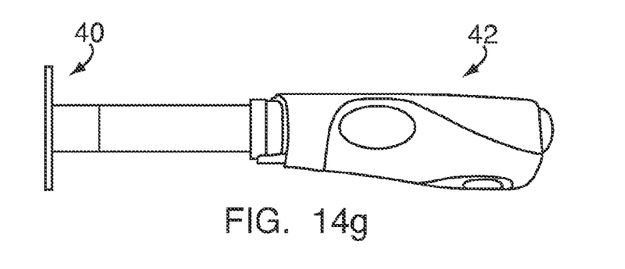

The injection aid 2 may also prevent improper use of a syringe 14. The syringe 14 is designed for use with insulin and other drugs that need to be injected into a recipient's fatty tissue or muscle. Because of the size of the disk 4, intravenous use of the syringe 14 is difficult. For example, as shown in FIG. 12, because of the disk 4, the needle 18 cannot be inserted into a vein at an angle, as is typically required for intravenous injections. In an embodiment where the injection aid 2 is permanently affixed to a syringe 14, an example of which is shown in FIG. 13, the injection device 30 may be designed to have the needle 18 break or permanently detach from the syringe body 32 if someone attempts to remove the permanently affixed disk 4, for rendering the injection device inoperable. The needle 18 may break based on its material strength, or the needle and/or disk and/or syringe body may be designed to have a weak spot or other frangible connection 34 for permanent detachment of at least the needle 18 from the syringe body 32 if suitable force is applied to the disk 4. As should be appreciated, the disk, needle, and/or syringe body may be configured for easy detachment of the needle in response to directional forces. For example, the components may be configured so that the needle does not easily detach upon application of a force in a direction along the axis "A" of the syringe, but that the needle will easily detach upon application of a net force generally perpendicular or offset from the axis, e.g., a force in the direction "A" or "B" as shown in FIG. 12. With a permanently attached injection aid 2/disk 4, the injection device 30 cannot be used for the intravenous injection of illegal drugs, which typically requires angling a needle into a surface blood vessel. Note that no other portions of the injection system are attached to the top surface proximate or coextensive with the disk's perimeter, and that extend back towards the syringe and contact (and/or are attached to) the syringe. This facilitates disablement of the syringe if someone attempts to remove the disk, e.g., the disk acts as a lever to break the syringe.

The injection aid 2 may be reusable. The injection aid 2 may be attached to a syringe or pen 14 and then removed after use. In another embodiment, the injection aid 2 may be a permanent fixture to a syringe 14 and would be disposed of after use.

The embodiments described above and shown in FIGS. 1-13 disclose an apparatus for helping a patient or caregiver with injection by syringe or pen. The injection aid is a disk with a central orifice surrounded by a flange, which attaches to the needle hub of a syringe or pen by the flange. The needle of the syringe or pen extends through the central orifice and allows injection into the skin. The disk prevents the recipient from seeing the needle and allows the needle to be inserted to the proper depth.

FIGS. 14a-14g show an embodiment of the injection aid 40 for use with an insulin pen 42. The injection aid 40 is generally similar to the injection aid 2, except that the flange 46 will typically have a wider inner diameter "D1" than the diameter "D2" of the central orifice 44 for fitting the injection end of an insulin pen 42.

In another embodiment, at least a portion of an outer surface of the disk 4 is colored a fluorescent color, for facilitating visual identification of the disk. By "fluorescent color" it is meant a color pigment that converts part of absorbed light energy into visible light of a different wavelength, thereby causing a glow-like vibrancy. The disk may also be phosphorescent, that is, "glow in the dark," based on the polymer material used for the disk, or through an application of phosphorescent paint applied to the disk.

An embodiment of the present invention may be characterized as an injection system that includes: (i) disposable syringe means 14, 16, 18, 42 for injecting a liquid into a body; and (ii) injection aid means 2, 40 attached to the syringe means for blocking a needle portion 18 of the syringe means from view, when the syringe is viewed generally from the rear.

The disk 4 is an annular, solid member lying perpendicular to the syringe longitudinal axis. The disk includes a flat bottom surface 12, and a top surface 10. If the top surface is also flat, the top and bottom surfaces will be parallel to one another. The top and bottom surfaces are connected by a cylindrical outer sidewall of the solid member. The disk extends radially outwards from the syringe hub, with the cylindrical sidewall defining the radially outermost extent of the disk. Typically, the disk will be connected to the flange only (for a detachable injection aid) or to the syringe hub only (integral injection aid). In another embodiment, the flat top and bottom surfaces define a longitudinal boundary of the annular outermost portion of the disk, with respect to the syringe longitudinal axis. That is to say, the outermost portion of the disk, proximate to the cylindrical sidewall, is flat, without any portions or elements extending past the top or bottom surface in the longitudinal direction of the syringe.

Although the present invention has been primarily illustrated as using a disk, guards with other shapes could be used instead (e.g., polygonal), provided they (i) define a flat contact surface 12 perpendicular the needle and (ii) extend generally uniformly radially outwards from the syringe, so that the needle is generally blocked from view, from the perspective of someone viewing the syringe generally from the end of the syringe opposite the needle.

In another embodiment, an injection system includes a disposable syringe and an injection aid. The injection aid includes a guard attached to an outlet end of the syringe, proximate to the syringe needle. The guard has a top surface, as well as a bottom contact surface that is perpendicular to the needle. The needle extends out past the contact surface by a fixed distance "L." The contact surface is flat, and no other portions of the injection system extend past the contact surface other than the needle. The guard extends all the way around the syringe, and extends radially outwards from a syringe longitudinal axis by an amount at least equal to the fixed distance that the needle extends past the contact surface. Thus, although the guard is not necessarily round, it encompasses an area around the syringe/needle axis defined by a radius$\geq$L. Typically, at least the outermost annular portion of the top surface, which defines the perimeter of the guard, is also flat. No other portions of the injection system are attached to the top surface proximate or coextensive with the perimeter, as extend back towards the syringe.

While the invention has been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed.

What is claimed is:

1. An injection system comprising:
 a syringe having a hub and a needle extending longitudinally outwards from the hub, said needle and hub being in a fixed relationship; and
 an injection aid comprising:
  a rigid guard attached to the syringe proximate to the hub, said guard having a flat first surface lying substantially perpendicular to the longitudinal axis of the syringe and needle and an annular flange attached to said guard, at least a portion of said hub engaging the flange and being disposed in an orifice defined by the flange;
 wherein the guard is a disk having a radius at least as great as said fixed distance;
 wherein said injection aid is removable from the syringe and is reusable;
 wherein the needle extends outwards from said first surface by a fixed distance, and wherein the guard extend radially outwards from the syringe hub by a second distance at least as great as said fixed distance, whereby the guard tends to block the needle from view of a user of the injection system.

2. The injection system of claim 1, wherein the syringe is a disposable syringe having a polymer body.

3. The system of claim 2, wherein the disk is an annular, solid member lying perpendicular to the syringe longitudinal axis and extending radially outwards from the hub, said solid member defining the first surface and a flat second surface, and said first and second surfaces being parallel to one another and connected by a cylindrical outer side wall of the solid member, wherein the side wall defines the radially outwards-most extent of the disk.

4. The system of claim 3, wherein the first and second surfaces define a longitudinal boundary, with respect to the syringe longitudinal axis, of an outer annular portion of the disk.

5. The system of claim 2, wherein the disk is an annular, solid member lying perpendicular to the syringe longitudinal axis, said solid member defining the first surface and a flat second surface, and said first and second surfaces being parallel to one another and connected by a cylindrical outer side wall of the solid member, wherein the first and second surfaces define a longitudinal boundary of an outer annular portion of the disk with respect to the syringe longitudinal axis.

6. The system of claim 2, wherein at least a portion of an outer surface of the disk is fluorescent-colored and/or phosphorescent, for facilitating visual identification of the disk.

7. An apparatus for helping a person with a needle-based injection device, comprising;
 a rigid guard having a central orifice, a flat bottom, and a top surface;
 a flange surrounding said central orifice and located on said top surface of said guard;
 wherein said guard is a disk;
 a syringe, wherein the syringe has an outlet end where a fixed needle is attached, said outlet end of said syringe being fixedly attached to said flange of said guard, wherein the needle extends through the central orifice;
 wherein the guard extends substantially radially beyond the flange and the syringe for blocking the needle from view of a user of the syringe;
 wherein the guard and flange are non-removably connected to each other; and
 wherein the guard and flange are removable from the syringe.

8. The apparatus of claim 7, wherein the syringe is a disposable syringe having a polymer body.

9. The apparatus according to claim 8, wherein the disk is fluorescent-colored and/or phosphorescent, for facilitating visual identification of the disk.

10. The apparatus according to claim 8, wherein said disk has a diameter of about 1.25 inches.

11. The apparatus according to claim 8, wherein said disk includes an annular recess surrounding said central orifice and located on said bottom surface of said disk.

12. The apparatus according to claim 8, wherein said disk has a diameter as least twice as great as an outer diameter of said flange.

13. An injection system comprising:
 a disposable syringe having an elongate polymer body with an outlet end and a fixed needle attached to and extending longitudinally outwards from said outlet end; and
 an injection aid comprising:
  a rigid guard having an orifice, a top surface, and a flat surface lying substantially perpendicular to the longitudinal axis of the syringe; and a flange at least partially surrounding said orifice and attached to the top surface of the guard, wherein the outlet end of said syringe is attached to the flange, with the needle extending through the central orifice and longitudinally outwards past the flat guard surface;

wherein the guard extends radially outwards from the flange and outlet end of the syringe, and wherein the line defined by the distal tip of the needle and a radially outermost edge of the guard forms an angle of at least 45 degrees with respect to the needle, whereby the needle tends to be blocked from view when the syringe is viewed from the rear;

wherein said guard is a disk;

wherein the injection aid is removable from said syringe and said injection aid is reusable.

* * * * *